(12) United States Patent
Poirier et al.

(10) Patent No.: US 7,754,499 B2
(45) Date of Patent: Jul. 13, 2010

(54) SEMI-CONTINUOUS BLOOD SEPARATION USING MAGNETIC BEADS

(75) Inventors: Michael Poirier, Vista, CA (US); Vijay Mahant, Murrieta, CA (US)

(73) Assignee: Qualigen, Inc., Carlsbad, CA (US)

( * ) Notice: Subject to any disclaimer, the term of this patent is extended or adjusted under 35 U.S.C. 154(b) by 595 days.

(21) Appl. No.: 11/693,658

(22) Filed: Mar. 29, 2007

(65) Prior Publication Data

US 2007/0231888 A1 Oct. 4, 2007

Related U.S. Application Data

(60) Division of application No. 09/977,930, filed on Oct. 11, 2001, now Pat. No. 7,214,544, which is a continuation-in-part of application No. 09/949,314, filed on Sep. 7, 2001, now Pat. No. 6,821,790, which is a continuation-in-part of application No. 09/514,686, filed on Feb. 28, 2000, now Pat. No. 6,291,249, which is a continuation-in-part of application No. 09/261,068, filed on Mar. 2, 1999, now abandoned.

(51) Int. Cl.
*G01N 33/543* (2006.01)

(52) U.S. Cl. ...................................... 436/523
(58) Field of Classification Search .................. None
See application file for complete search history.

(56) References Cited

U.S. PATENT DOCUMENTS

| | | | |
|---|---|---|---|
| 4,594,327 A | 6/1986 | Zuk | |
| 4,663,029 A | 5/1987 | Kelland et al. | |
| 4,710,472 A | 12/1987 | Saur et al. | |
| 4,753,776 A | 6/1988 | Hillman et al. | |
| 5,169,789 A | 12/1992 | Bernstein | |
| 5,766,552 A | 6/1998 | Doshi et al. | |
| 5,863,502 A * | 1/1999 | Southgate et al. | ............ 422/58 |
| 6,291,249 B1 | 9/2001 | Mahant et al. | |

* cited by examiner

*Primary Examiner*—Ann Y Lam
(74) *Attorney, Agent, or Firm*—Fish & Associates, PC

(57) ABSTRACT

A container having a flexible wall receives a continuous flow of a biological fluid that includes a target antigen and emits a continuous flow of the biological fluid at least partially depleted from the target antigen. The container further comprises a compartment with magnetic beads coupled to an affinity marker that binds the target antigen, and the target antigen is separated from the biological fluid using a magnetic force and an automatic mechanical force, wherein at least one of the magnetic force and automatic mechanical force is transmitted through the flexible wall.

5 Claims, 1 Drawing Sheet

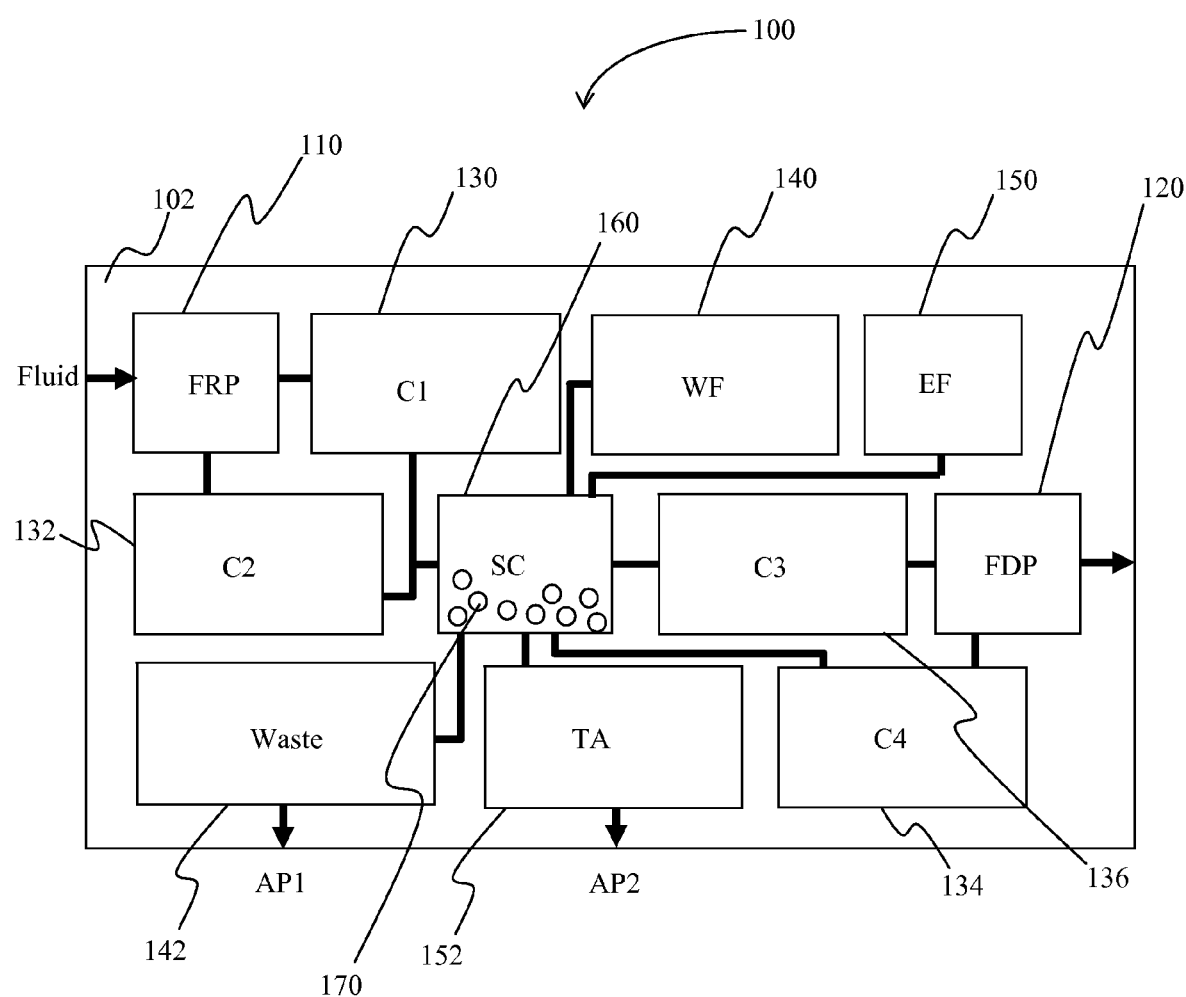

SEMI-CONTINUOUS BLOOD SEPARATION USING MAGNETIC BEADS

This application is a divisional application of previously allowed U.S. patent application Ser. No. 09/977,930 filed on Oct. 11, 2001 now U.S. Pat. No. 7,214,544 which is a C-I-P of U.S. patent application Ser. No. 09/949,314, filed Sep. 7, 2001, now U.S. Pat. No. 6,821,790 which is a C-I-P of U.S. patent application Ser. No. 09/514,686 filed Feb. 28, 2000, now U.S. Pat. No. 6,291,249, which is a C-I-P of U.S. patent application Ser. No. 09/261,068 filed Mar. 2, 1999 abandoned Jul. 31, 2000, all of which are incorporated herein by reference in their entirety.

FIELD OF THE INVENTION

The field of the invention is blood separation.

BACKGROUND OF THE INVENTION

Separation, and especially on line separation of target antigens from biological fluids for diagnostic and/or curative purposes is often desirable, especially where the biological fluid is a whole blood or other bodily fluid. Among frequently isolated and/or separated target antigens are diseased cells (e.g., T4-helper cells infected with HIV virus), non-diseased cells (e.g., adult stem cells), various bacteria, and viruses.

There are numerous methods of on line separation or isolation of target antigens known in the art, and such methods may be grouped into one of two categories. For example, in a discontinuous separation, a biological fluid is isolated from a source (e.g., blood is drawn from a human) and subsequently processed for the desired target antigen. Most commonly, such methods include centrifugation for relatively large volumes of biological fluids, or magnetic separation for relatively small volumes. In either case, the processed fluid may then be reintroduced into the human. While discontinuous separation is generally relatively effective, various disadvantages remain. Among other things, processing of the isolated biological fluid typically requires transfer of the fluid among a multitude of containers, which significantly increases the likelihood of contamination of the processed sample. Furthermore, depending on the particular the volume of the isolated fluid, multiple samples need to be drawn for sufficient amount of target antigen.

On the other hand, in a continuous separation, a biological fluid is directly routed from a source (e.g., via i.v. line) into a separation unit and continuously processed for the desired target antigen before the depleted fluid is rerouted into the source. Most commonly, such methods include gradient centrifugation, or on line magnetic separation. While discontinuous separation is generally advantageous with respect to simplified sample handling, all or almost all of the on line separations require relatively expensive and intricate equipment. Consequently, many continuous separation methods and configurations present various challenges. For example, continuous centrifugation equipment (e.g., as the equipment used in thrombocytophoresis) typically requires control by highly trained professionals. For magnetic separation, cells or other target antigens are separated by virtue of their magnetic moment, thereby typically limiting separation efficiency at desirable flow rates.

Although various configurations and methods for isolation and/or separation of one or more components from blood are known to the art, all or almost all of them suffer from one or more disadvantage. Therefore, there is a need to provide apparatus and methods for improved isolation and/or separation of components from blood.

SUMMARY OF THE INVENTION

The present invention is directed to apparatus and methods for a container having at least one flexible wall, a fluid receiving port, a fluid discharge port, and a plurality of compartments fluidly coupled to at least one of the fluid receiving port and the fluid discharge port. The fluid receiving port in contemplated containers receives a continuous flow of a biological fluid that includes a target antigen, and the fluid discharge port emits a continuous flow of the biological fluid that is at least partially depleted from the target antigen, wherein at least one of the compartments further comprises a plurality of magnetic beads that are coupled to an affinity marker that binds the target antigen, and wherein the target antigen is separated from the biological fluid using a magnetic force and an automatic mechanical force, wherein at least one of the magnetic force and automatic mechanical force is transmitted through the flexible wall.

In one aspect of the inventive subject matter, one or more of the compartments include a buffer, a wash fluid, an isotonic fluid, and/or an elution fluid, and at least one of the compartments may further include a port that allows draining of the least one of the compartment.

In a further aspect of the inventive subject matter, the affinity marker is selected from the group consisting of an antibody, an antibody fragment, and a lectin, and particularly preferred biological fluids comprise whole blood. It is further preferred that the target antigen is selected from the group consisting of a stem cell, a diseased cell, a bacterium, and a virus.

Various objects, features, aspects and advantages of the present invention will become more apparent from the following detailed description of preferred embodiments of the invention, along with the accompanying drawing.

BRIEF DESCRIPTION OF THE DRAWING

The drawing is a schematic illustration of an exemplary container according to the inventive subject matter.

DETAILED DESCRIPTION

It is generally contemplated that a target antigen is separated and/or isolated from a biological fluid in a container with a flexible wall in a semi-continuous fashion using magnetic beads via an automated mechanical force and a magnetic force.

More particularly, it is contemplated that a container has at least one flexible wall, a fluid receiving port, a fluid discharge port, and a plurality of compartment fluidly coupled to at least one of the fluid receiving port and the fluid discharge port, wherein the fluid receiving port receives a continuous flow of a biological fluid that includes a target antigen, and wherein the fluid discharge port emits a continuous flow of the biological fluid that is at least partially depleted from the target antigen, wherein at least one of the compartments further comprises a plurality of magnetic beads that are coupled to an affinity marker that binds the target antigen, and wherein the target antigen is separated from the biological fluid using a magnetic force and an automatic mechanical force, wherein at least one of the magnetic force and automatic mechanical force is transmitted through the flexible wall. As used herein, the term "continuous flow" refers to the flow of the fluid in and out of the container during operation, and includes any flow rate above 0.1 ml/min. Typical continuous flow rates are generally in the range between 1-100 ml/min, but may also be less than 1 ml/min (e.g., 0.1 ml/min to 1 ml/min), or even higher than 100 ml/min, especially where the container is relatively large. In less preferred aspects, however, it is contemplated that the flow may also be discontinuous (i.e., the flow rate may be intermittently below 0.1 ml/min).

The general concept of magnetic separation using an automated mechanical force and a magnetic force is disclosed in commonly owned U.S. Pat. No. 6,291,249 and U.S. patent application Ser. No. 09/261,068 filed Mar. 2, 1999, both of which are incorporated herein by reference. The drawing depicts an exemplary container 100 having a flexible top sheet 102 laminated to a back sheet (not shown). The term "flexible" as used herein refers to a quality of material characterized in that the material can be deformed to a significant degree without destruction. For example, a soft plastic foil is considered flexible, while a hard plastic or glass plate is not considered flexible under the scope of this definition. A fluid receiving port 110 that receives the biological fluid is fluidly coupled to compartments 130 and 132, which are in turn fluidly coupled to separation chamber 160. Separation chamber 160 includes a plurality of magnetic beads 170, and at least some of the beads are coated with an affinity marker (not shown). Separation chamber 160 is further fluidly coupled to the following compartments: Compartment 140 (e.g., containing wash fluid), compartment 150 (e.g., containing elution fluid), compartment 142 (e.g., for receiving waste fluid), compartment 152 (e.g., for receiving eluted target antigen), and compartments 134 and 136. Compartments 134 and 136 are further fluidly coupled to fluid discharge port 120. Additional ports AP1 and AP2 are fluidly coupled to compartment 142 and 152, respectively, and allow draining of the fluid and/or target antigen from the compartments.

With respect to the container 100 it should be appreciated that the container may be fabricated from various materials. For example, it is generally preferred that the container is fabricated from a flexible back sheet and a flexible top sheet, and that all compartments and fluid conduits that fluidly couple one compartment to another compartment are formed by the top and bottom sheet. However, in alternative aspects, the back sheet may be inflexible, while only the top sheet is flexible. Moreover, it should be appreciated that while it is preferred that the entire top sheet is flexible, in alternative containers only portions of the top sheet are flexible. In still further contemplated aspects, at least a portion of the top sheet and/or bottom sheet may be transparent (e.g., to perform optical measurements, including scatter, absorption and/or transmission). Thus, at least one of the compartments and the conduits will include a flexible portion through which flow of the fluid in the compartment and/or conduit can be controlled, initiated, or stopped by pressing an actuator or other mechanical device thereon. However, it is generally preferred that the entire container is flexible, and may therefore be stored in a roll or otherwise non-flat configuration.

It should further be appreciated that the volume of the various compartments in contemplated containers may vary considerably, and a particular volume will generally depend on the particular separation and/or isolation procedure. For example, where the target antigen is a Hepatitis C virus (frequently present at relatively high loads), the volume of the compartments may be between about 1-3 ml (or less) and about 4-20 ml, and more. On the other hand, where the target antigen is a particular set of leukocytes, suitable volumes of the compartments may be between about 5-10 ml (or less) and about 20-100 ml, and more. Still further, it should be recognized that where volumes of particular fluids are exceeding the volume of the appropriate compartment, additional ports (see e.g., AP1 and AP2) may be included through which excess volume my be drained or added.

Furthermore, it is contemplated that while at least some of the compartments may comprise a fluid (which may be employed to wash, dilute, and/or elute a target antigen from the magnetic bead), other compartments may be empty prior to operation of the container. For example, it is preferred that the compartment 130, 142, 152, and 134 are empty to receive the biological fluid when the process is initiated. Preferred containers may further include adhesive labels, permanent labels, bar codes, etc., to encode test and patient data, and may have additional channels or other means for proper alignment with an instrument that receives the container and delivers the automatic mechanical force and the magnetic force.

It is further contemplated that the conduits that fluidly couple the compartments are configured such that an actuator or other mechanical device may compress the conduit to partially or completely stop flow of the fluid through the conduit. In preferred containers, at least one, more typically several, and most typically all of the fluid conduits are at least temporarily sealable (i.e., flow of the fluid through the conduit can be stopped). Alternatively, or additionally, contemplated conduits may include jet valves, Venturi valves, or other means that restrict the flow of fluid in a unidirectional manner, or allow flow of fluid only above a predetermined pressure. There are numerous such means known in the art, and all of those are contemplated suitable for use herein.

With respect to the magnetic beads, it is preferred that such beads comprise a paramagnetic composition embedded in synthetic polymers or cellulose. Although paramagnetic particles are preferred, the coated particles can also or alternatively include ferromagnetic or chromium material or mixtures thereof. In still further variations, suitable particles can be coated with many other materials including natural or synthetic polymers, agarose etc. The preferred particle size is in the range of 0.1-100 micrometers, but alternative sizes between 10-100 micrometers or larger than 100 micrometers are also contemplated. Viewed from another aspect, it is contemplated to employ particles having a mean volume between about $5 \times 10^{-24}$ $m^3$ and about $5 \times 10^{-6}$ $m^3$. The term "coated" is used herein to mean any complete or partial covering of any exposed surface. It should further be appreciated that by employing magnetic beads in a compartment that can be fluidly isolated from other compartments, separation of the target antigen bound to the magnetic bead will occur in a quasi-stationary manner. Viewed from another perspective, it should be appreciated that the separation using contemplated containers is not based on a separation using a magnetic moment of a magnetic particle in a flow of a biological fluid.

In further preferred aspects of the inventive subject matter, contemplated beads are coated with polyclonal or monoclonal antibodies or antibody fragments that have a binding specificity towards the target antigen. Therefore, suitable antibodies or antibody fragments particularly include commercially available preparations. However, it should be recognized that contemplated affinity markers may also include non-protein affinity molecules and may therefore include nucleic acids, biotin, lectins, etc. Thus, contemplated target antigens include proteins, nucleic acids, avidin-labeled samples, viruses, bacteria, and healthy (stem cells) and diseased cells (infected cells).

Consequently, it is contemplated that depending on the particular nature of the target antigen at least one of the compartments (e.g., 152) may operate as a compartment to isolate a target antigen, or to separate a target antigen for further reaction. For example, it is contemplated that in such a compartment various biochemical reactions may be performed. Especially contemplated reactions include chromogenic reactions and PCR (with predispensed reagents in the compartment). Therefore, it should also be recognized that at least one compartment of the container may be heated, cooled, agitated, or illuminated.

In an exemplary operation, it is contemplated that a continuous flow of a biological fluid is provided (e.g., via an i.v. line powered by a peristaltic pump) to the fluid receiving port 110 and compartment 130, both of which will act as a temporary reservoir for the incoming biological fluid, while a predetermined amount of a predispensed buffer or biological fluid previously directed to compartment 132 is directed (e.g., via actuators or other hydraulic pressure) to the separation compartment that includes a plurality of magnetic beads to which an affinity marker is coupled. Once compartment 132 is (at least partially) emptied, compartment 132 may act (optionally in conjunction with FRP 110) as a temporary reservoir for the incoming biological fluid, and the biological fluid in compartment 130 is directed towards the separation compartment.

It is further contemplated that the target antigen in the fluid in compartment 160 will bind to the affinity markers 170 on the magnetic beads, and it is still further contemplated that the magnetic beads (and with this the target antigens) will be retained compartment 160 by a magnet (in a position proximal to compartment 160, not shown) while the remainder of the biological fluid is passed on to at least one of compartment 134 and 136. In an optional wash step, the target antigen may now be washed with a wash fluid from compartment 140 and the spent wash fluid may then be directed to a waste compartment 142. The target antigen may then be removed from the magnetic beads 170 using an elution fluid from compartment 150, and the eluted target antigen is collected in compartment 152. It should be particularly appreciated that all of the target antigen separation and/or isolation steps may be performed while compartment 110 and at least one of the compartments 130 and 132 continuously receive the biological fluid.

Once the biological fluid (now depleted from the target antigen) is directed to 134 and/or 136, a new separation cycle may be initiated. Furthermore, it should be appreciated that by employing at least 2 compartments (here: 134 and 136) in fluid communication with the fluid discharge port 120, a continuous discharge of depleted biological fluid is achieved. For example, while the depleted fluid from 136 and 120 is discharged (e.g., directed back to the source of the biological fluid), compartment 134 can be filled at the same time, and will therefore provide continuous flow of depleted biological fluid once 136 is (at least partially) emptied. Alternatively, additional compartments may be included to receive a fluid within the container as temporary reservoirs.

With respect to the automatic mechanical force, it is generally preferred that at least one, and more preferably a plurality of actuators that compress respective compartments to provide actuation of the fluid. It is further preferred that at least one, and more typically some or all of the conduits that fluidly couple the compartments will be configured such that an actuator pressing on such a conduit will prevent flow of the fluid from one compartment to another compartment. Still further it is contemplated that one or more compartments may include a port or opening that allows draining or refill of the compartment.

Thus, specific embodiments and applications of semi-continuous blood separation using magnetic beads have been disclosed. It should be apparent, however, to those skilled in the art that many more modifications besides those already described are possible without departing from the inventive concepts herein. The inventive subject matter, therefore, is not to be restricted except in the spirit of the appended contemplated claims. However, it should be appreciated that claims in a non-provisional application based on this provisional application may be entirely different or different in part. Moreover, in interpreting the specification, all terms should be interpreted in the broadest possible manner consistent with the context. In particular, the terms "comprises", and "comprising", should be interpreted as referring to elements, components, or steps in a non-exclusive manner, indicating that the referenced elements, components, or steps may be present, or utilized, or combined with other elements, components, or steps that are not expressly referenced.

What is claimed is:

1. A container for continuously separating whole blood, comprising:
    a flexible top sheet and a flexible bottom sheet configured to form top and bottom of the container;
    wherein the container further comprises a fluid receiving port, a fluid discharge port, and a plurality of compartments fluidly coupled to at least one of the fluid receiving port and the fluid discharge port;
    wherein at least two of the plurality of compartments are in fluid communication with the fluid discharge port;
    wherein at least two of the of compartments are in fluid communication with the fluid discharge port and configured such that one of the two can be filled with a first fluid while the other of the two is being depleted of a second fluid;
    wherein the container is further configured such that a target antigen can be separated from the whole blood within at least one of the plurality of compartments using a magnetic force and an automatic mechanical force, wherein at least one of the magnetic force and automatic mechanical force is transmitted through the flexible top sheet; and
    wherein at least one of the compartments further comprises a plurality of magnetic beads that carry an affinity marker that binds the target antigen.

2. The container of claim 1 wherein the container is configured to allow a plurality of actuators in a device retaining the container to compress at least some of the compartments in a predetermined manner to thereby move the whole blood and processed whole blood through the plurality of compartments.

3. The container of claim 1 wherein a plurality of compartments and fluid conduits that fluidly couple one compartment to another compartment are formed by the top and bottom sheet.

4. The container of claim 1 wherein at least one of the compartments further includes a port that allows draining of the at least one of the compartments.

5. The container of claim 1 wherein at least one of the compartments or a conduit that fluidly couples one compartment to another compartment is configured such that an actuator can compress the at least one of the compartments or conduit to partially or completely stop flow of the whole blood or processed whole blood through the conduit or compartment.

* * * * *